US006160107A

United States Patent [19]
Targoff et al.

[11] Patent Number: 6,160,107
[45] Date of Patent: Dec. 12, 2000

[54] NUCLEIC ACIDS ENCODING ANTIGENS ASSOCIATED WITH POLYMYOSITIS AND DERMATOMOSITIS

[75] Inventors: Ira N. Targoff; Qun Ge, both of Oklahoma City, Okla.

[73] Assignees: Oklahoma Medical Research Foundation, Oklahoma City; Board of Regents of the University of Oklahoma, Norman, both of Okla.

[21] Appl. No.: 07/975,902

[22] Filed: Nov. 10, 1992

Related U.S. Application Data

[63] Continuation of application No. 07/579,023, Sep. 7, 1990, abandoned.
[51] Int. Cl.[7] .............................. C07H 21/04; C12Q 1/68; G01N 33/00
[52] U.S. Cl. .......................... 536/23.5; 536/24.31; 435/6; 436/94
[58] Field of Search ................................ 435/6; 536/23.5, 536/24.31, 23.4

[56] References Cited

U.S. PATENT DOCUMENTS 4,711,955  12/1987  Ward et al. ................................ 536/29

FOREIGN PATENT DOCUMENTS 12462   6/1989   WIPO .

OTHER PUBLICATIONS

Blaszczyk, M., et al., "Autoantibodies to Nucleolar Antigens in Systemic Scleroderma: Clinical Correlations," *British Journal of Dermatology*, 123:421–430 (1990).

M. Blüthner, E. Genth and F. Bautz, "Cloning of a cDNA–Fragment Coding for an Epitope Recognized by Anti–PM/Scl–Autoantibodies," Abstract from the First International Workshop on the Molecular and Cell Biology of Autoantibodies and Autoimmunity, Heidelberg, Federal Republic of Germany, (Springer–Verlag Jul. 27–29, 1989).

Bradford, M.M., "A Rapid and Sensitive method for the Quantitation of Microgram Quantities of Protein Utilizing the Principle of Protein–Dye Binding," *Analytical Biochemistry*, 72:248–254 (1976).

Devereux, J., et al., "A Comprehensive Set of Sequence Analysis Programs for the VAS," *Nucleic Acids Research*, 12(1):386–395 (1984).

Frohman, M.A., et al., "Rapid Production of Full–length cDNAs from Rare Transcripts: Amplification Using a Single Gene–specific Oligonucleotide Primer," *Proc. Natl. Acad. Sci. USA*, 85:8998–9002 (1988).

Ge. Targoff, et al., "Molecular Cloning of an Antigenic Component of the PM–SCL Antigen," *Abstracts of Scientific Presentations*, 33(9): (Sep. 1990).

Gelpi, C., et al., "Identification of Protein Components Reactive with Anti–PM/Scl Autoantibodies," *Clin. exp. Immunol.* 81:59–64 (1990).

Genth, E., et al., "Immunogenetic Associations of Scleroderma–related Antinuclear Antibodies," *Arthritis and Rheumatism*, 33(5):657–665 (1990).

Laemmli, U.K., "Cleavage of Structural Proteins During the Assembly of the Head of Bacteriophage T4," *Nature*, 227:680–685 (1970).

Loh, E.Y., et al., "Polymerase Chain Reaction with Single–Sided Specificity: Analysis of T Cell Receptor δ Chain," *Science*, 243:217–220 (1989).

F. Miller, S. Twitty, T. Biswas and P. Plotz, "Origin and Regulation of a Disease–Specific Autoantibody Response: Antigenic Epitopes, Spectrotype Stability, and Isotype Restriction of Anti–Jo–1 Autoantibodies," *The Journal of Clinical Investigation 85:* 468–475 (Feb. 1990).

Mimori, T., "Scleroderma–Polymyositis Overlap Syndrome," *International Journal of Dermatology*, 26(7):419–425 (1987).

Nilasena, D.S., et al., "Molecular Cloning of the Dermatomyositis (DM)–Associated Mi–2 Antigen," *Official Journal of the American College of Rheumatology*, 33(9) (1990).

Nilasena, D.S., et al., "Biochemical Analysis of the Dermatomyositis Autoantigen MI2," 1990 ASBMB/AAI Abstract Form.

M. Nishikai and M. Reichlin, "Heterogeneity of Precipitating Antibodies in Polymyositis and Dermatomyositis," *Arthritis and Rheumatism* 23(3): 881–888 (Aug. 1980).

M. Nishikai and M. Reichlin, "Purification and Characterization of a Nuclear Non–Histone Basic Protein (Mi–1) which Reacts with Anti–Immunoglobulin Sera and the Sera of Patients with Dermatomyositis," *Molecular Immunology* 17: 1129–1141 (1980).

Oddis, C.V., et al., "The Association of HLA Class II Alleles with Autoantibody to PM–SCL," *American College of Rheumatology*, 34(5) (1991).

Plotz, P.H., et al., "Current Concepts in the Idiopathic Inflammatory Myopathies: Polymyositis, Dermatomyositis, and Related Disorders," *Annals of Internal Medicine*, 111(2):143–157 (1989).

Pollard, K.M., et al., "Autoantibodies in Scleroderma," *Clinical and Experimental Rheumatology*, 7/S–3:57–62 (1989).

M. Reichlin and F. Arnett, "Multiplicity of Antibodies in Myositis Sera," *Arthritis and Rheumatism* 27(10): 1150–1156 (Oct. 1984).

(List continued on next page.)

*Primary Examiner*—Bradley L. Sisson
*Attorney, Agent, or Firm*—Arnall Golden & Gregory, LLP

[57] ABSTRACT

Proteins including at least one epitope of the Mi-2 antigen, which are used for the diagnosis of dermatomyositis, and proteins including at least one epitope of the PM-Scl antigen, which are used for the diagnosis of polymyositis, particularly polymyositis-scleroderma overlap disorders are provided in an easily purified form for use in immunoassays and purification of the associated autoantigens. DNA that encode these proteins and that may also be used in diagnostic assays or as probes to obtain related DNA are also provided.

8 Claims, 16 Drawing Sheets

OTHER PUBLICATIONS

M. Reichlin, I. Targoff, et al., "Antibodies to a Nuclear/Nucleolar Antigen in Patients with Polymyositis Overlap Syndromes," *Journal of Clinical Immunology* 4(1): 40–44 (1984).

M. Reichlin and M. Mattioli, "Description of a Serological Reaction Characteristic of Polymyositis," *Clinical Immunology and Immunopathology* 5: 12–20 (1976).

G. Reimer, U. Scheer, J. Peters, and E. Tan, "Immunolocalization and Partial Characterization of a Nucleolar Autoantigen (PM–Sc1) Associated with Polymyositis/Scleroderma Overlap Syndromes," *Journal of Immunology* 137(12): 3802–3808 (Dec. 15, 1986).

G. Reimer and V. Steen, et al., "Correlates Between Autoantibodies to Nucleolar Antigens and Clinical Features in Patients with Systemic Sclerosis (Scleroderma)," *Arthritis and Rheumatism* 31(4): 525–532 (Apr. 1988).

Sanger, F., et al., "DNA Sequencing with Chain–terminating Inhibitors," *Biochemistry,* 72(12:5463–5467 (1977).

Tabor, S., et al., "DNA Sequence Analysis with a Modified Bacteriophage T7 DNA Polymerase," *Proc. Natl. Acad. Sci. USA, Biochemistry,* 84:4767–4771 (1987).

E. Tan, "Antinuclear Antibodies: Diagnostic Markers for Autoimmune Diseases and Probes for Cell Biology," *Advances in Immunology* 44:93–151 (Academic Press, New York 1989).

I. Targoff, "Autoantibodies to Aminoacyl–Transfer RNA Synthetases for Isoleucine and Glycine: Two Additional Synthetases are Antigenic in Myositis," *The Journal of Immunology* 144(5): 1737–1743 (Mar. 1, 1990).

Targoff, I.N., et al., "Clinical Features and Immunologic Testing of Patients with Anti–MI–2 Antibodies," *Arthritis and Rheumatis,* 33(7–12):S72 (1990).

Targoff, I.N., "Dermatomyositis and Polymyositis," *Curr. Probl. Dermatol.,* 134–180 (1991).

I. Targoff, "Immunologic Aspects of Myositis," *Current Opinion in Rheumatology* 1: 432–442 (1989).

Targoff, I.N., "Inflammatory Muscle Disease," *The Lung in Rheumatic Diseases,* 303–328 (1990).

Targoff, I.N., "Laboratory Manifestations of Polymyositis/Dermatomyositis," *Laboratory Manifestations,* 6(2): 76–92 (1988).

I. Targoff, G. Raghu and M. Reichlin, "Antibodies to Mi–1 in SLE: Relationship to Other Precipitins and Reaction with Bovine Immunoglobulin," *Clinical Experimental Immunology* 53:76–82 (1983).

I. Targoff and M. Reichlin, "The Association Between Mi–2 Antibodies and Dermatomyositis," *Arthritis and Rheumatism* 28(7): 796–803 (Jul. 1985).

I. Targoff and M. Reichlin, "Humoral Immunity in Polymyositis and Dermatomyositis," *The Mount Sinai Journal of Medicine* 55(6): 487–493 (Nov. 1988).

Targoff and M. Reichlin, "Immunological Aspects," *Inflammatory Diseases of Muscle,* 37–70 (1988).

I. Targoff and M. Reichlin, "Measurement of Antibody to Jo–1 by ELISA and Comparison to Enzyme Inhibitory Activity," *The Journal of Immunology* 138(9): 2874–2882 (May 1, 1987).

I. Targoff and M. Reichlin, "Nucleolar Localization of the PM–Scl Antigen," *Arthritis and Rheumatism* 28(2): 226–230 (Feb. 1985).

Towbin, H., et al., "Electrophoretic Transfer of Proteins from Polyacrylamide Gels to Nitrocellulose Sheet: Procedure and Some Applications," *Proc. Natl. Acad. Sci. USA,* 76(9):4350–4354 (1979).

E. Treadwell, M. Alspaugh, J. Wolfe, and G. Sharp, "Clinical Relevance of PM–1 Antibody and Physiochemical Characterization of PM–1 Antigen," *The Journal of Rheumatology* 11(5): 658–662 (1984).

J. Wolfe, E. Adelstein and G. Sharp, "Antinuclear Antibody with Distinct Specificity for Polymyositis," *Journal of Clinical Investigation* 59: 176–178 (Jan. 1977).

Young & Davis, "Efficient Isolation of Genes Using Antibody Probes", Proc. Natl. Acad. Sci. USA, vol. 80, pp. 1194–1198, Mar. 1983.

Sanger, et al., "DNA Sequencing with Chain–Terminating Inhibitors", Proc. Natl. Acad. Sci. USA, vol. 74, No. 12, pp. 5463–5467, Dec. 1977.

Blüthner, et al. First Int. Workshop on the Mol. and Cell Biol. of Autoantb. and Autoimm., Heidelberg (Springer–Verlag Jul. 27–29, 1989).

Targoff, et al. *Arthritis and Rheum.* 28: 796–803 (1985).

*Nucleic Acids Research,* vol. 17, No. 16, 1989, p. 6749.

*J. Biochem* 98, 1395–1403 (1985) see computer generated sequence comparison.

*Nucleic Acids Research,* 17, 9993–10013, (1989), see computer generated sequence comparison.

*J. Mol. Endocrinol.* 1, 5–11 (1988), see computer generated sequence comparison.

*J. Biol. Chem.,* 257, 11078–11086 (1982), see computer generated sequence comparison.

FIG. 1A

```
GAA TTC CGG CTA GGG CTT CTG GGT GGC AAG AGG AAG AAA GGA GGC
Glu Phe Arg Leu Gly Leu Leu Gly Gly Lys Arg Lys Lys Gly Gly
                 15              30              45

TCG AGC GAC GAA GGT CCT GAA CCA GAG GCT GAG GAA TCA GAC CTG
Ser Ser Asp Glu Gly Pro Glu Pro Glu Ala Glu Glu Ser Asp Leu
                 60              75              90

GAC AGT GGC AGT GTC CAC AGT GCC TCA GGC CGG CCT GAT GGC CCT
Asp Ser Gly Ser Val His Ser Ala Ser Gly Arg Pro Asp Gly Pro
                105             120             135

GTC CGC ACC AAG AAA CTA AAG AGA GGC CGG CCA GGA AGG AAG AAG
Val Arg Thr Lys Lys Leu Lys Arg Gly Arg Pro Gly Arg Lys Lys
                150             165             180

AAG AAG GTC CTG GGC TGT CCT GCA GTG GCC GGG GAG GAG GAG GTT
Lys Lys Val Leu Gly Cys Pro Ala Val Ala Gly Glu Glu Glu Val
                195             210             225
```

FIG. 1B

```
GAT GGC TAC GAG ACG GAT CAC CAG GAT TAC TGT GAG GTG TGC CAG   270
Asp Gly Tyr Glu Thr Asp His Gln Asp Tyr Cys Glu Val Cys Gln

CAG GGT GGG GAA ATT ATT CTG TGT GAC ACC TGC CCT CGT GCC TAC   315
Gln Gly Gly Glu Ile Ile Leu Cys Asp Thr Cys Pro Arg Ala Tyr

CAC CTC GTC TGC CTT GAT CCT GAG CTT GAC CGG GCT CCA GAG GGC   360
His Leu Val Cys Leu Asp Pro Glu Leu Asp Arg Ala Pro Glu Gly

AAA TGG AGC TGC CCT CAC TGT GAG AAG GGG GTC CAG TGG GAG       405
Lys Trp Ser Cys Pro His Cys Glu Lys Gly Val Gln Trp Glu

GCC AAG GAG GAA GAA GAA TAC GAA GAG GAG GAG GAG GAA GAA GAG   450
Ala Lys Glu Glu Glu Glu Tyr Glu Glu Glu Glu Gly Glu Glu Glu
```

FIG. 1C

```
                                          465                     480                     495
GGG GAG AAG GAG GAG GAT GAT CAC ATG GAG TAC TGC CGC GTA
Gly Glu Lys Glu Glu Asp Asp His Met Glu Tyr Cys Arg Val 510                     525                     540
TGC AAG GAC GGC GGG GAG CTC CTG TGT GAC GCG TGC ATC TCC
Cys Lys Asp Gly Gly Glu Leu Leu Cys Asp Ala Cys Ile Ser 555                     570                     585
TCC TAC CAC ATT CAT TGT CTA AAC CCT CTG CCT GAC ATT CCC
Ser Tyr His Ile His Cys Leu Asn Pro Leu Pro Asp Ile Pro 600                     615                     630
AAT GGT GAA TGG CTG TGT CCC CGA TGC ACA TGC CCC GTG CTG AAG
Asn Gly Glu Trp Leu Cys Pro Arg Cys Thr Cys Pro Val Leu Lys 645                     660                     675
GGT CGA GTG CAG AAG ATC CTA CAT TGG CGG TGG GGG GAG CCA CCT
Gly Arg Val Gln Lys Ile Leu His Trp Arg Trp Gly Glu Pro Pro
```

FIG. 1D

```
                                                      690                    705                            720
GTA GCA GTG CCA GCC CCT CAA CAG GCA GAT GGA AAT CCA GAT GTC
Val Ala Val Pro Ala Pro Gln Gln Ala Asp Gly Asn Pro Asp Val 735                    750                            765
CCA CCC CCC CGT CCT CTT CAA GGC AGA TCA GAG CGA GAG TTC TTT
Pro Pro Pro Arg Pro Leu Gln Gly Arg Ser Glu Arg Glu Phe Phe 780                    795                            810
GTC AAG TGG GTA GGA CTA TCC TAC TGG CAC TGC TCC TGG GCC AAG
Val Lys Trp Val Gly Leu Ser Tyr Trp His Cys Ser Trp Ala Lys 825                    840                            855
GAG CTT CAG CTG GAA ATC TTC CAT TTG GTT ATG TAT CGA AAC TAC
Glu Leu Gln Leu Glu Ile Phe His Leu Val Met Tyr Arg Asn Tyr 870                    885                            900
CAG CGG AAG AAT GAC ATG GAT GAG CCC CCA CCC CTG GAC TAT GGC
Gln Arg Lys Asn Asp Met Asp Glu Pro Pro Pro Leu Asp Tyr Gly
```

FIG. 1E

```
TCC GGC GAG GAT GGG AAG AGC GAC AAG CGT AAA GTG AAA GAC
Ser Gly Glu Asp Gly Lys Ser Asp Lys Arg Lys Val Lys Asp
        915             930             945

CCG CAC TAT GCT GAG ATG GAG GAG AAG TAC TAT CGT TTT GGC ATC
Pro His Tyr Ala Glu Met Glu Glu Lys Tyr Tyr Arg Phe Gly Ile
        960             975             990

AAG CCA GAG TGG ATG ACC GTC CAC CGC ATC ATC AAC CAC AGT GTG
Lys Pro Glu Trp Met Thr Val His Arg Ile Ile Asn His Ser Val
        1005            1020            1035

GAT AAA AAG GCC GGA ATT
Asp Lys Lys Ala Gly Ile
        1050
```

FIG. 2A

```
       15                30                45                60
GGGTTTTACCGAAGTTTCCTGGCTTCCAAGCATTTGCGAAACACAGGGAGACAGGTTG
CCCAAAAATGGCTTCAAAAGGACCGAAGGTTCGTAAAACGCTTTGTGTCCCTCTGTCCAAC 75                90               105               120
CTTCAGTGCATGAGCAGAGAGTAATGCAGTACCATGGGTGTCGCAGCAACATTAAGGATCGA
GAAGTCACGTACTCGTCTCATTACGTCATGGTACCCACAGCGTCGTTGTAATTCCTAGCT 135               150               165               180
AGTAAAAGTGACTGAGCTGGAAGACAAGTTTGATTACTAGTTGATGCCAATGATGTAATT
TCATTTCACTGACTCGACCTTCTGTTCAAACTAAATGATCAACTACGGTTACTACATTAA 195               210               225               240
CTGGAGAGAGTGGGTATTTTACTGGATGAAGCCCTCAGGTGTAAACAAGAATCAACAGCCT
GACCCTCTCACCCATAAAATGACCTACTTCGGAGTCCACATTTGTTCTTAGTTGTCGGA
```

FIG. 2B

```
         15                30                45                60
GGGTGTACAAAAGCAGCACCAGCATTTGGTTGTCCGGTCCACAGGGCGCCACGTGTCTTCC
CCCACACATGTTTTCGTCGTGGTCGTAAACCAACAGGCCAGGTGTGTCCCGCGGTGCACAGAAGG
         75                90               105               120
AGGACTATCTCTGTGTCCAGTTGTACCTGAAGCCCTCTGTCTGACTTTCCAGTTGGAAAGG
TCCTGATAGAGACACAGGTCAACATGGACTTCGGAGACAGACTGAAAGGTCAACCTTTCC
        135               150               165               180
ACATGCTTTTGTTTCCCACCGACTGTTTAATTTTTTTGGCTGCAATGCATTTCTTGCCAG
TGTACGAAAACAAAGGGTGGCTGACAAATTAAAAAAAAACCGACGTTACGTAAAGAACGGTC
        195               210               225               240
ACGGGGTCTGTTTATTTGGATCAAACTGAGAAGAAACTTTGGATTTGCTGTTTCCAGCAA
TGCCCCAGACAAATAAACCTAGTTTGACTCTTCTTTGAAACCTAAACGACAAAGGTCGTT
        255               270               285
AAGCCCTTGAAGTCTGACTGGCTGTAGTCGTAAGGGCGTAAACTCTTTTC
TTCGGAACTTCAGACTGACCGACATCAGCATTCCGCATTTGAGAAAAAG
```

RESTRICTION ENZYME MAP OF THE INSERT OF CLONE JH2 CODING FOR A PORTION OF THE PM-SCL PROTEIN

```
0      0.5      1.0      1.5      2.0      2.5 a      b c    d e           f    g h
```

Numbers indicate points along cDNA strand.
Letters indicate restriction enzyme digestion sites.

Taq I cleaves at a and b.

Xho I cleaves at c.

Sma I cleaves at d and g.

Pst I cleaves at e and h.

Kpn I cleaves at f.

FIG. 3B

Fragments were derived from double digestions with either TaqI + KpnI (Fragments I, II, III, and IV) or XhoI and PstI (fragments V, VI, VII, and VIII).

```
                        Approx size
0 to a = fragment I.      350 bp
a to b = fragment II.     450 bp
b to f = fragment III.    950 bp
f to 2.5 = fragment IV.   750 bp 0 to c = fragment V.      900 bp
c to e = fragment VI.     325 bp
e to h = fragment VII.    825 bp
h to 2.5 = fragment VIII. 450 bp
```

FIG. 4A

Partial Sequence of Fragment I (from 0 toward a):

```
  1            11           21           31           41
AATTCGGGTT   TTACCGAAGT   TTTCCTGGCT   TCCAAGCATT   TTGCGAAACA 51           61           71           81           91
CAGGGAGACA   GGTTGCTTCA   GTGCATGAGC   AGAGTAATGC   AGTACCATGG 101          111          121          131          141
GTGTCGCAGC   AACATTAAGG   ATCGAAGTAA   AGTGACTGAG   CTGGAAGACA 151          161          171          181          191
AGTTTGATTT   ACTAGTTGAT   GCCAATGATG   TAATTCTGGA   GAGAGTGGGT 201          211          221
ATTTTACTGG   ATGAAGCCTC   AGGTGTAA
```

Partial Sequence of Fragment I, Opposite strand (from a toward 0):

FIG. 4B

```
  1           11          21          31          41
CGAAACTTGA  GCTGAGGTCG  GATGATATTT  TTTGCATGAA  GCAGCCGGAA 51          61          71          81          91
AGTTTCAGAT  TTTGCTTTTT  TGCCATATtC  TGCTGCCTTA  CGGTTCCAGC 101         111         121         131         141
TGGACACTAC  CGTTTTGGGG  ACCTGCAAGC  CGGCAGGAGG  ACAGGCTGTT 151         161         171         181
GATTCTTGTT  TACACCCTGAG GCTTCATCCA  GTAAAATACC
```

Partial Sequence of Fragment II (direction not yet determined):

```
  1           11          21          31          41
CGAGAGAAGA  TTGCAATNCC  AACACACCAT  TTCTTCCTAA  AATCTTCATC
```

FIG. 4C

```
51            61            71            81            91
AAACCCCAATG   CTCAGAAACC    TCTCCCTCAA    GCTCTCTCTA    AGGAAAGGCG 101           111           121           131           141
GGAACCGACA    GGATCGTCTG    AGGACTTGGA    CGTCCCCCCT    GCACTGGCTG

151
ATTT
```

Partial Sequence of Fragment II, Opposite Strand (opposite direction):

```
1             11            21            31            41
GCTCGGTACC    CCGAGGGTGT    CAATGATGAA    GTCTTCCGTC    GAGTAGAAAT 51            61            71            81
TTGCATCAGG    CAGGTCAGTC    CAGGAAGCTC    GTTAAGAGT
```

FIG. 4D

Partial Sequence of Fragment III (from b toward f):

```
1            11           21           31           41
AGCAAGTTAT   NTTTTTTTCA   TCAGGGAAGA   GGCTCGCCTG   CTTCTGAACT 51           61           71           81           91
GGCACAGATC   CACTGGTTGG   GATGATTGGA   TAGCCATCCG   GAGGgCATGG

101
GAGCgTC
```

Partial Sequence of Fragment III, opposite strand (from f toward b):

```
1            11           21           31           41
GAGAGCCTCA   CAGACCCAGC   CATCGTTAAG   GTCTTTCATG   GTGCTGATTC 51           61           71           81           91
AGACATAGAA   TGGCTACAGA   AAGACTTTGG   GTTGTATGTA   GTAAACATGT
```

FIG. 4E

```
101         111         121         131         141
TTGATACTCA  TCAGGCAGCA  CGCTTCTTAA  CTGGGCAGGC  ACTCACTCGA
151         161         171         181
TCATCTCCTG  AAACTCTACT  GCAACGTGGA  CTCAAC
```

Partial Sequence of Fragment IV (from f toward end):

```
1           11          21          31          41
CACNTGCCTG  ATTCCACAGC  TGTCATCACN  TTATTTAATg  AACCTAGTGC
51          61          71          81          91
TGAAGACAGT  AAAAAGGGTC  CATTGACAGT  TGCACAgAAA  AAAgCCCAgA
101
A
```

FIG. 4F

Partial Sequence of Fragment IV, opposite strand (end toward f):

```
  1           11          21          31          41
GCAGCACCAG  CATTTGGNGT  NTCCGGTCCA  CAGGGCGCCAC  GTGTCTTCCA 51          61          71          81          91
GGACTATCTC  TGTGGCCAGT  TGTACCTGAA  GCCTCTGTCT  GACTTTCCAG 101         111         121         131
TTGGAAAGGA  CATGCTTTTg  tTcCCACCGA  CTGTTTAA
```

Partial Sequence of Fragment VI (direction not determined):

```
  1           11          21          31          41
GCTGCACGNN  TGCCTTGCCG  CGCTCCCACA  TNTCCAgCCT  CATTTgTCA 51          61          71          81
TAGATATATA  GCAGgTAATG  GGtGTCATCC  C
```

FIG. 4G

Partial Sequence of Fragment VI, Opposite strand (opposite direction):

```
  1           11          21          31          41
  GCTTCGAAGT  GACATGTACA  TTCTCAATGA  GAGCCTCACA  GACCCAGCCA
 51           61          71          81          91
  TCGTTAAGGT  CTTTCATGGT  GCTGATTCAG  ACATAGAATG  GCTACAGAAA
101          111
  GACTTTGGGT  TG
```

NUCLEIC ACIDS ENCODING ANTIGENS ASSOCIATED WITH POLYMYOSITIS AND DERMATOMOSITIS

This is a continuation of U.S. Ser. No. 07/579,023 by Ira N. Targoff and Qun Ge, filed Sep. 7, 1990.

BACKGROUND OF THE INVENTION

This invention is directed to human antigens that can be used for the diagnosis of myositis and myositis-overlap syndromes that have an autoimmune pathogenesis.

Autoimmune disorders arise when the immune system reacts against its own tissues. Autoimmune diseases are often classified on the basis of whether a single organ or tissue is involved or whether multiple organs or tissues are involved. Generalized or systemic autoimmune diseases, such as systemic lupus erythematosus (hereinafter SLE), which are characterized by the involvement of multiple organs and tissues, are often associated with the presence of autoantibodies to fundamental cellular components. Other autoimmune diseases are characterized by autoantibodies to antigens associated with a single organ or tissue.

Systemic autoimmune diseases are typically characterized by the presence of autoantibodies. Some of the autoantibodies associated with the particular disease may be disease specific and others may be common to many autoimmune diseases. For example, SLE, which is a prototypical immune disorder, is characterized by the presence of autoantibodies that are detectable in other autoimmune disease, such as anti-single-strand DNA antibodies, anti-histones antibodies, and anti-ribonuclear particle (RNP) antibodies, and also by the presence of autoantibodies that are SLE-specific, such the as anti-double-stranded DNA antibodies. Other systemic autoimmune disorders, such as rheumatoid arthritis and idiopathic inflammatory myopathies, are also characterized by the presence of autoantibodies in the sera of patients that react with fundamental nuclear and cytoplasmic intracellular components. As with SLE, some of these autoantibodies are associated with other autoimmune disorders and some are specifically associated with autoimmune myositis.

The idiopathic inflammatory myopathies polymyositis, dermatomyositis and the related overlap syndromes disorder, such as polymyositis-scleroderma overlap, are inflammatory myopathies that are characterized by chronic muscle inflammation and proximal muscle weakness. The muscle inflammation causes muscle tenderness, muscle weakness, and ultimately muscle atrophy and fibrosis (see, e.g., Plotz, et al. *Annals of Internal Med.* 111: 143–157 (1989)). Also associated with the muscle inflammation are elevated serum levels of aldolase, creatine kinase, transaminases, such as alanine aminotransferase and aspartate aminotransferase, and lactic dehydrogenase. Other systems besides muscle can be affected by these conditions, resulting in arthritis, Raynaud's phenomenon, and interstitial lung disease. Clinically, polymyositis and dermatomyositis are distinguished by the presence of a characteristic rash in patients with dermatomyositis. Differences in the myositis of these conditions can be distinguished in some studies of muscle pathology.

Autoantibodies can be detected in about 90% of patients with polymyositis and dermatomyositis (Reichlin and Arnett, *Arthritis and Rheum.* 27: 1150–1156 (1984)). Sera from about 60% of these patients form precipitates with bovine thymus extracts on Ouchterlony immunodiffusion (ID), while sera from other patients stain tissue culture substrates, such as HEp-2 cells, by indirect immunofluorescence (IIF) (see, e.g., Targoff and Reichlin *Arthritis and Rheum.* 28: 796–803 (1985); Nishikai and Reichlin *Arthritis and Rheum.* 23: 881–888 (1980); Reichlin, et al., *J. Clin. Immunol.* 4:40–44 (1984)). There are numerous precipitating autoantibody specificities in myositis patients, but each individual antibody specificity occurs in only a fraction of the patients.

Many autoantibodies associated with myositis or myositis-overlap syndromes have been defined, and, in some cases, the antibodies have been identified. These include antibodies that are present in other disorders and also disease-specific antibodies (see, e.g., (Targoff and Reichlin *Mt. Sinai J. of Med.* 55: 487–493 (1988)). Characteristic antibodies and their respective specificities are listed in Table 1. For example, a group of myositis-associated autoantibodies have been identified which are directed at cytoplasmic proteins that are related to tRNA and protein synthesis, particularly aminoacyl-tRNA synthetases. These include anti-Jo-1, which is the most common autoantibody associated with myositis autoimmune disorders (about 20% of such patients (Nishikai, et al. *Arthritis Rheum.* 23: 881–888 (1980)) and which is directed against histidyl-tRNA synthetase; anti-PL-7, which is directed against threonyl-tRNA synthetase; and anti-PL12, which is directed against alanyl-tRNA synthetase. Anti-U1 RNP, which is frequently found in patients with SLE, may also be found in mixed connective tissue disease, overlap syndromes involving myositis, or in some cases of myositis alone. This antibody reacts with proteins that are uniquely present on the U1 small nuclear ribonucleoprotein, which is one of the nuclear RNPs that are involved in splicing mRNA. Autoantibodies such as anti-Sm, anti-Ro/SSA, and anti-La/SSB, that are usually associated with other conditions, are sometimes found in patients with overlap syndromes. Anti-Ku has been found in myositis-scleroderma overlap syndrome and in SLE. The Ku antigen is a DNA binding protein complex with two polypeptide components, both of which have been cloned.

Anti Jo-1 and other anti-synthetases are disease specific. Other myositis-associated antibodies are anti-PM-Scl, which is present in about 5–10% of myositis patients, many of whom have polymyositis-scleroderma overlap, and anti-Mi-2, which is present in about 8% of myositis patients, almost exclusively in dermatomyositis. Mi-2 is found in high titer in about 20% of all dermatomyositis patients and in low titer in less than 5% of polymyositis patients (see, e.g., Targoff and Reichlin, *Mt. Sinai J. of Med.* 55: 487–493 (1988)).

Anti-Mi was first described by Reichlin and Mattioli, *Clin. Immunol. and Immunopathol.* 5: 12–20 (1976)). A complement-fixation reaction was used to detect it and, in that study, patients with dermatomyositis, polymyositis and polymyositis overlap syndromes had positive reactions. The prototype or reference serum, from patient Mi, forms two precipitin lines on immunodiffusion (ID) with calf thymus antigens, Mi-1 and Mi-2. Mi-1, which has been purified from bovine thymus nuclear extracts (Nishikai, et al. *Mol. Immunol.* 17: 1129–141 (1980)) is rarely found in other sera and is not myositis specific (Targoff, et al., *Clin. Exp. Immunol.* 53: 76–82 (1983)).

Anti-Mi-2 was found to be a myositis-specific autoantibody by Targoff, et al. *Arthritis and Rheum.* 28: 796–803 (1985). Furthermore, all patients with the antibody have the dermatomyositis rash. It is therefore potentially important as a diagnostic tool and, perhaps, ultimately as a tool for understanding the disease etiology. Anti-Mi-2 is also the only antibody response that appears to be selective for dermatomyositis and not for other subgroups of polymyositis without skin involvement.

Bovine thymus Mi-2 antigen was originally found to be a nuclear protein that separates in SDS polyacrylamide (SDS-PAGE) gels into two bands with apparent molecular weights of 53 kilodaltons (hereinafter kDa) and 61 KDa, respectively. Recently, additional higher molecular weight bands have been found. The bovine thymus antigenic activity is destroyed by SDS-PAGE and is trypsin sensitive, but not RNAse sensitive (Targroff et al. *Arthritis and Rheum.* 28: 796–803 (1985)). Its nature and function have not as yet been identified.

Anti-PM-1 was first identified as an antibody found in 61% of dermatomyositis/polymyositis patients, including patients; with polymyositis-scleroderma overlap (Wolfe, et al. *J. Clin. Invest.* 59: 176–178 (1977)). PM-1 was subsequently shown to be more than one antibody. The unique specificity component of PM-1 was later named PM-Scl (Reichlin, et al. *J. Clin. Immunol.* 4: 40–44 (1984)). Anti-PM-Scl is found in the sera of about 5–10% of myositis patients, but is most commonly associated with polymyositis-scleroderma overlap syndrome. It also occurs in patients with polymyositis or dermatomyositis alone or in patients with scleroderma without myositis.

Anti-PM-Scl antibody immunoprecipitates a complex from HeLa cell extracts of at least eleven polypeptides that have molecular weights ranging from about 20 to 110 kDa (see, Reimer, et al., *J. Immunol.* 137:3802–3808 (1986). The antigen is trypsin-sensitive, occurs in nucleoli (see, e.g., Targoff and Reichlin *Arthritis Rheum.* 28: 226–230 (1985)) and is believed to be a preribosomal particle.

In an abstract, Blüthner, et al., *First Int. Workshop on the Mol. and Cell Biology of Autoantibodies and Autoimmunity* in Heidelberg (Springer-Verlag July 27–29, 1989) report that sera from patients suffering from polymyositis/scleroderma-overlap syndrome (PM/Scl) recognize two major nucleolar proteins of 95 and 75 kDa molecular weight in Western blots of a Hela cell extract. They also report that cDNA that encodes a 20 kDa protein reactive with autoantibodies eluting from the 95 kDa PM-Scl HeLa antigen subunit has been cloned from a HeLa cDNA library. The sequence of the cloned DNA has not as yet been reported.

TABLE 1

Autoantibodies to Nuclear and cytoplasmic Antigens in Dermatomyositis and Polymyositis Patients[1]

| Antibody | % of Patients | Characteristic Subgroup |
| --- | --- | --- |
| Group A | | |
| Anti-Jo-1 (his-tRNA synthetase) | 18 | PM-ILD |
| Anti-PM-Scl | 8 | PM-Scleroderma |
| Anti-Mi-2 | 8 | DM |
| Anti-Ku | <1 | Overlap |
| Anti-PL-7 (thr-tRNA synthetase) | 3 | PM-ILD |
| Anti-PL-12 (ala-tRNA-synthetase) | 3 | PM-ILD |
| Anti-SRP (signal recognition particle) | 3 | PM |
| Anti-Fer, Mas, etc. (other tRNA associated antigens) | rare | PM |

TABLE 1-continued

Autoantibodies to Nuclear and cytoplasmic Antigens in Dermatomyositis and Polymyositis Patients[1]

| Antibody | % of Patients | Characteristic Subgroup |
| --- | --- | --- |
| Group B | | |
| Anti-nRNP (U1 small nuclear RNP) | 13 | Overlap |
| Anti-Ro/SS-A | 7 | Overlap |
| Ro/SSA + La/SSB | 2 | Sjögren's, SLE |
| Anti-mitochondrial | 24 | — |
| Anti-cytoskeletal | 86 | all |

[1]Targoff and Reichlin (1988), Mt. Sinai J. of Med. 55:487–493, 488.
PM, polymyositis.
DM, dermatomyositis.
ILD, interstitial lung disease.
Group A - autoantibodies that are usually found in serum from patients with myositis or myositis overlap syndromes.
Group B - more common in other conditions, but also occurring in PM/DM.

These antibodies serve as useful diagnostic markers because of their high specificity for myositis and its subgroups. At the present time, however, it is difficult and time consuming to routinely screen sera for the presence of these antibodies because standard serum needed for comparison is not widely available and highly concentrated tissue extracts must be used. Both anti-PM-Scl and anti-Mi-2 give only weak reactions in immunodiffusion, making them even more difficult to detect. In addition, these screening assays generally use the corresponding bovine antigen (which is more readily available for clinical purposes), which may not detect the presence of autoantibodies that do not cross-react sufficiently to be detectable. Further, the relatively insensitive immunodiffusion technique is used.

There is, thus, a need to obtain the human myositis-specific antigens, such as the Mi-2 antigen and the PM-Scl antigen, in purified form so that rapid, accurate, and convenient diagnostic assays can be developed. Recent studies with other antigens such as anti-Jo-1 have indicated a correlation of antibody level with disease activity, as reported by Miller, et al., *J. Clin. Invest.* 85:468–475 (1990). Quantitative assays for these antibodies may help assess disease activity if similar findings are observed for these antibodies. In addition, elucidation of the biochemical structure and function of the particular disease-specific antigen at which the immune response is directed may aid in understanding the etiology of the disease and in the development of effective treatments. Also, since these antigens are conserved cellular proteins, they are likely to be functionally important proteins. Study and identification of these antigens may provide significant insights into nuclear and nucleolar processes.

It is therefore an object of this invention to provide DNA encoding antigens that are specifically recognized by myositis-specific autoantibody which can be expressed in large quantities and easily purified.

It is a further object of the invention to provide human antigens or portions thereof for use in diagnostic assays and as tools for studying autoimmune myositis.

It is another object of the invention to provide methods for detecting autoantibodies that are uniquely found in the sera of individuals with dermatomyositis or myositis-scleroderma overlap.

SUMMARY OF THE INVENTION

Immunoassays for detecting myositis specific antibodies which will help in diagnosis of dermatomyositis (DM), polymyositis (PM), and myositis-sclerosis overlap are provided. Isolated DNA molecules that encode Mi-2 and PM-Scl antigens or antigenic portions thereof, DNA probes for isolating cDNA or genomic DNA clones that encode such antigens or portions thereof, the antigens encoded by the isolated DNA, and diagnostic assays for detecting anti-Mi-2 and anti-PM-Scl autoantibodies in sera are also provided.

DNA that encodes a protein that includes at least one epitope of the human Mi-2 antigen and DNA that encodes a protein that includes at least one epitope of the 100 kDa subunit of the human PM-Scl antigen have been cloned from a human cDNA library. This DNA can be used to provide proteins that include the human Mi-2 and PM-Scl epitopes which can be used in assays for autoantibodies to these epitopes, or for other purposes. In addition, this DNA is used to provide probes to screen cDNA and genomic libraries in order to isolate DNA that encodes additional portions of the human antigens or DNA that spans each gene, or to obtain DNA that encodes related antigens in humans and other mammals. The DNA that encodes additional portions of the antigens, and the proteins encoded thereby, may be used in immunodiagnostic assays in order to identify patients that express anti-Mi-2 autoantibodies that do not react with the originally cloned epitopes.

The DNA encoding the Mi-2 antigen, or the antigen, are useful in immunodiagnostic assays, including ELISAs, dot blots, immunodiffusion, radioimmunoassays and immunoprecipitation assays, to detect anti Mi-2 to help in diagnosing dermatomyositis. The DNA encoding Pm-Scl antigen, or the antigen, are useful in similar assays to help in diagnosing polymyositis and polymyositis-scleroderma overlap disorders.

BRIEF DESCRIPTION OF THE DRAWINGS

FIG. 1 sets forth the nucleotide sequence and corresponding protein sequence of the 1.1 KB insert of clone L1 that encodes at least one epitope of the human Mi-2 antigen.

FIG. 2 sets forth portions of the nucleotide sequence of the 2.5 KB insert of clone JH2 that encodes at least part of the 100 kDa protein of the human PM-Scl antigen. The two sequences, FIGS. 2A and 2B, respectively, represent sequences from the opposite ends of the 2.5 KB insert. Double-stranded sequencing from pUC19 was used.

FIGS. 4A–4E show partial nucleotide sequences for fragments defined in FIG. 3, as determined by sequencing in a single direction.

FIG. 4A is the partial sequence of Fragment I of FIG. 3 (from 0 toward a) and the opposite strand (from a toward 0).

FIG. 4B is the partial sequence of Fragment II of FIG. 3 (direction not yet determined) and the opposite strand (opposite direction).

FIG. 4C is the partial sequence of Fragment III of FIG. 3 (from b toward f) and the opposite strand (from f toward b).

FIG. 4D is the partial sequence of Fragment IV of FIG. 3 (from f toward end) and the opposite strand (from end toward f).

FIG. 4E is the partial sequence of Fragment VI of FIG. 3 (direction not determined) and the opposite strand (opposite direction).

DETAILED DESCRIPTION OF THE INVENTION

Figure 3A:
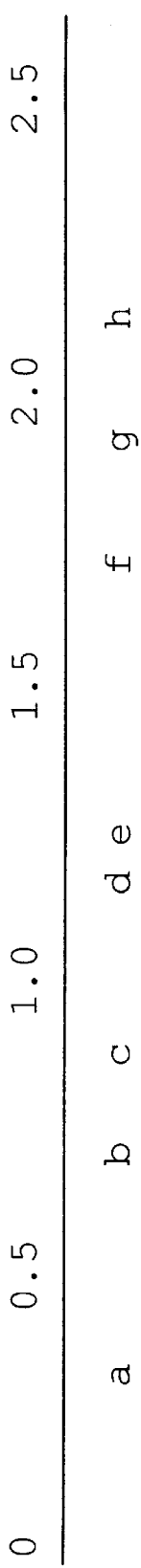
FIG. 3 is a restriction enzyme map of clone JH2 showing the location of cleavage sites for TaqI, RpnI, XhoI, and SmaI, and PstI. Fragments from double digestions with KpnI and TaqI; and XhoI and PstI, are defined.

Characteristics of the myositic-specific antigens.
Identification and Characterization of the PM-Scl antigen.

The PM-Scl antigen was originally defined by a standard serum containing antibody that reacted with a previously undefined antigen in immunodiffusion against bovine tissue extract. Immunodiffusion can determine unequivocally by reactions of identity that two sera contain antibodies to the same antigen even when that single antigen is mixed with thousands of others in a concentrated tissue extract. A reaction of non-identity can determine that two sera react with different antigens. PM-Scl antigen was defined as the antigen in tissue extracts that reacts with the standard anti-PM-Scl serum. A second serum has anti-PM-Scl if it shows a reaction of identity with the standard serum (or a known positive validated by reaction of identity with the standard serum) in immunodiffusion.

Bovine PM-Scl antigen is PM-Scl antigen derived from bovine tissue. Human PM-Scl antigen is PM-Scl antigen derived from human tissue. It is expected that it will be better to use human antigen for testing since it is known that more patients react with human Ro/SSA antigen than react with bovine Ro/SSA. Reaction of anti-Jo-1 with human Jo-1 is also stronger than with bovine Jo-1.

The human PM-Scl antigen appears to be a particle consisting of at least eleven polypeptides, as determined by immunoprecipitation by Reimer, et at. *J. Immunol.* 137: 3802–3808 (1986). The PM-Scl antigen has not been purified. Anti-PM-Scl antibody immunoprecipitates from HeLa cell extract a complex of between eleven and thirteen polypeptides that have molecular weights ranging from about 20 to 110 kDa, as discussed in the background of the invention. The antigen is trypsin-sensitive, occurs in nucleoli and is believed to be a preribosomal particle.

Characteristics of the Mi-2 antigen.

Since anti-Mi-2 is specific for dermatomyositis, assays that detect the presence of these antibodies in human serum are useful for diagnosing dermatomyositis. Standard immunoassays, such as ELISAs, Ouchterlony immunodiffusion and other assays that are known to those of skill in the art, provide a useful repertoire for such diagnosis. The purified human Mi-2 antigens, peptides that include at least one epitope that is recognized by the respective autoantibodies and/or DNA that encodes at least one such epitope are, therefore, preferred components for any accurate and reliable diagnostic assay.

Bovine Mi-2 antigen has an apparent molecular weight of two to three million, when measured using fast protein liquid chromatography gel filtration (FPLC). This is more than ten times the molecular weight of the largest band seen on SDS-PAGE gels of the antigen, which suggests that the purified bovine antigen is a complex of multiple copies of the components or a multimeric aggregate of many identical protein complexes that dissociate in SDS. SDS-PAGE of the immunoprecipitated human and purified bovine Mi-2 antigens indicates that both antigens are a complex consisting of multiple subunit proteins.

When purified by affinity chromatography, SDS-PAGE of the bovine antigen shows a high molecular weight band in the region of 200–240 kDa, and a band at 150 kDa. A very strong band is seen at 107 kDa and another at 40 kDa. When the preparation is separated by gel filtration on FPLC, the 200 and 40 kDa bands are seen in the same fraction, indicating that they are complexed. This fraction is active in ELISA. The 150 kDa band and 107 kDa band are not as consistently active in ELISA. No bands are active by Western blot against anti-Mi-2 sera.

The human antigen has not been purified. The human antigen has been analyzed by immunoprecipitation using HeLa cell extracts. A high molecular weight band in the 200–240 kDa range was again seen, and 150 kDa band is sometimes seen. Bands at 62 kDa and 65 kDa are usually seen, but a 40 kDa band is not seen. The most consistent band seen by immunoprecipitation from HeLa extract is 200 kDa. A similar band is seen with the bovine antigen but is less prominent than the 40 kDa band. There is no reaction with HeLa extract in Western blot by anti-Mi-2 sera. Thus, the high molecular weight bands of approximately 200 kDa are shared by bovine and HeLa forms of Mi-2 and may be the crucial components.

It is possible that one or more of the other components are degradation products. When the bovine antigen is subjected to affinity purification, the high molecular weight bands and the 40 kDa molecular weight band remain together, while the two lower molecular weight bands are separated. Because protease inhibitors do not affect the amounts of the lower molecular weight bands, it is likely that the lower molecular weight bands are independent components of the Mi-2 complex, which is dissociated in reducing conditions, rather than proteolytic breakdown products of the higher molecular weight proteins. The pattern of bands observed on the SDS polyacrylamide gels is reproducible and consistent for antigen prepared using the same immunosorbent column and also for antigen that is purified using IgG derived from sera from different patients. It is, therefore, probable that all of the observed bands in the purified antigen relate to Mi-2.

The antigenicity of the protein subunits of the bovine Mi-2 antigen is most consistently associated with the fractions of immunoaffinity purified antigen and FPLC purified antigen that include the proteins of molecular weights of 249, 198, 152 and 40 kDa. Bands similar to the three highest molecular weight bands are also seen on $^{35}$S-methionine-labeled immunoprecipitates from HeLa cell extracts. Western blots of the separated proteins, however, do not react with any antibodies in any sera that has been tested. This suggests that the reactive epitope in the antigen is conformational and is not present in the denatured and reduced form of the antigen complex. Alternatively, it is possible that the epitope is composed of more than one peptide and that dissociation of a complex of proteins destroys the immunoreactivity. Because all anti-Mi-2 autoantibodies that have been identified share this property, they may share common epitopes. The reaction of Mi-2 autoantibodies in immunodiffusion assays indicate that these antibodies must recognize multiple epitopes, since immune precipitation requires lattice formation.

The human and bovine Mi-2 antigens must be sufficiently similar for at least some autoantibodies against Mi-2 that are present in human sera to cross-react with the bovine Mi-2 antigen. Since the bovine and human Mi-2 antigens appear to include different subunits, as analyzed by different methods as described above, it is possible that a percentage of patients that might have autoantibodies that react with Mi-2 are not identified with assays that use bovine thymus extract. This is particularly significant with respect to Mi-2, since the epitope that is recognized by autoantibodies appears to be conformationally dependent and the subunit structure of the human antigen differs from that of the bovine antigen.

The human and bovine PM-Scl antigens and the human and bovine Mi-2 antigens are antigenically related since at least some autoantibodies against each of these antigens that are present in human sera react with the corresponding bovine antigen. However, it is unknown whether the autoantibodies of all individuals with anti-PM-Scl or anti-Mi-2 cross react with the corresponding bovine antigens and whether unique epitopes exist on the human antigens.

It is expected that diagnostic assays that employ the human antigens or proteins that include at least one epitope of the antigens as the diagnostic reagent will be more specific and reliable than similar assays that use bovine thymus nuclear extracts as the diagnostic reagent and may be useful for diagnosing myositis in patients whose myositis-specific autoantibodies do not react with the bovine antigen.

Cloning of DNA that encodes at least one epitope of Human myositis-specific antigens, Pm-Scl and Mi-2.

In order to obtain the human Mi-2 and PM-Scl antigens, or proteins that include at least one epitope thereof, in sufficient quantity for use in diagnostic assays, DNA that encodes all or a portion of each antigen has been cloned. Since the human antigens have not been purified and are not well-characterized, probes based on the protein sequence cannot be prepared nor can assays for the protein be devised, since biological activities of the antigens are unknown.

Sera that contain only autoantibody to Mi-2 antigen and sera that contain only autoantibody to PM-Scl antigen have been painstakingly collected at the University of Oklahoma Health Science Center, Oklahoma City, Okla., over the course of many years. In addition, sera from over 500 other patients with either DM or PM have been collected. Most of these sera have been tested for the various myositis autoantibodies. This very large and unique collection of sera, in particular of anti-Mi-2 sera, was essential in identifying cDNA for anti-Mi-2 and anti-PM-Scl.

An advantage of the cloned antigens is the ease of preparation of the antigen for use in ELISA. ELISA has advantages over other techniques for quantitation of antibody, which can be used to determine antibody titer and correlation with disease activity, if any. The cloned antigen can also be used to simplify detection of the antigen in a dot blot assay, which cannot be done with whole extract. A dot blot assay can be modified to a "dip-stick" type of test to make it even more simple and incorporate it into a test for multiple specificities at once.

In order to clone DNA that encodes the human Mi-2 and PM-Scl antigens, a human expression library was screened with sera that contains anti-Mi-2 autoantibodies and also with sera that contains anti-PM-Scl autoantibodies. Clones with DNA that encodes a protein reactive with the screening serum was selected.

The cloned DNA may be used in methods for diagnosing myositis or related conditions and for expressing portions of the myositis-specific antigens that react with antibodies that do not cross react with the bovine antigens.

Assays using the cloned proteins and the nucleic acids encoding the proteins.

The cloned and expressed proteins.

Once the clones that encode proteins reactive with anti-Mi-2 sera and/or anti-PM-Scl sera have been isolated, they can be expressed using methods known to those skilled in the art. The expressed proteins can be used in immunoblot assays, such as dot blot assays, including any solid phase assay in which the antigenic reagent is transferred to nitrocellulose prior to reaction with the test sample. The antigen reagent may be dotted directly onto the nitrocellulose or electrophoresed into a gel and transferred to the nitrocellulose.

Dot blot assays are more useful than conventional Western blot assays for testing reactions with epitopes that are conformationally dependent since it does not involve denaturing gels. In a dot blot assay, the reactive protein or peptide is dissolved or suspended in a non-denaturing buffered solution and spotted onto nitrocellulose filters until a sufficient amount is bound to the nitrocellulose to bind to any antibodies that may be present in low concentration. Alternatively, host cells, such as *E. coli* or eukaryotic cells (either mammalian cells or yeast cells), that contain DNA that encodes the protein or peptide that includes at least one epitope, are incubated under conditions whereby the protein is expressed. Typically, the cells are then gently lysed, spun to remove cell debris, and the supernatant dotted on nitrocellulose prior to reaction with the test sample. Usually some purification of the expressed protein is required in order to remove possible confounding reaction with the protein of the host cell.

In either embodiment, the amount of antigen or lysate clotted onto the nitrocellulose is a function of the particular type of assay. If the purpose of the assay is merely detection of the antibody, then, in order to drive the reaction, an excess of antigen is bound to the nitrocellulose filter. The types of assays and the conditions under which each type must be run are known to those of skill in the art and are readily ascertainable by one of skill in the art.

Blots in which the antigen is first electrophoresed under denaturing conditions onto polyacrylamide gel, known to those of skill in the art as Western blots, are not useful for detecting antibodies that bind to conformationally dependent epitopes but are useful for identifying or characterizing by molecular weight a particular portion, component or subunit of an antigen to which an antibody binds. After electrophoresis, the proteins on the gel are transferred to nitrocellulose, by any method known to those of skill in the art, for example, as described by Towbin, et al. *Proc.Nat'l. Acad. Sci. USA* 76: 4350–4354 (1979).

After transfer from a gel or after dotting the antigen reagent onto the nitrocellulose, excess protein binding sites on the nitrocellulose are blocked by binding known proteins, such as 5% bovine dry non-fat milk, albumin or serum, that do not bind to the antigen reagent or the autoantibody. Methods and reagents for blocking are well-known to those of skill in the art. The blocked nitrocellulose is then incubated with the test sample under conditions whereby autoantibodies that recognize the epitope or epitopes present on the antigen form complexes with the antigen. The nitrocellulose is then washed and treated so that the complexes may be detected. Detection may be effected by any method known to those of skill in the art. For example, to detect human autoantibodies, a goat anti-human immunoglobulin antibody may be used in a form in which it is conjugated to an enzyme, usually alkaline phosphatase or horse-radish peroxidase, and then a substrate is added that will deposit permanent color at sites where enzyme is present, specific to the particular enzyme. For example, for alkaline-phosphatase, a BCIP-NBT substrate is often used. Any convenient label, such as a radiolabel or an enzyme, may be used.

The cloned antigens can also be used in ELISAs, using methods known to those skilled in the art.

Probes derived from the cloned DNA.

Using standard procedures that are well-known to those of skill in the art, DNA probes may be prepared from the selected clones and used to screen an appropriate human cDNA library. A clone, or a series of clones, that include DNA that spans the entire gene for each antigen may be selected. The DNA probes may also be used to screen a genomic library in order to obtain genomic DNA that encodes all or a portion of the antigen or to screen genomic or cDNA libraries from human or other mammals in order to obtain DNA that encodes proteins that include sequences of amino acid that are related to the human Mi-2 and Pm-Scl antigens or epitopes thereof. Any of this DNA may then be used to produce proteins that may be used in diagnostic assays, such as those described above.

Definitions.

Unless defined otherwise, all technical and scientific terms used herein have the same meaning as is commonly understood by one of ordinary skill in the art to which this technology belongs. All publications and U.S. patents referenced herein are specifically incorporated by reference thereto.

As used herein, immunodiagnostic assays include assays that in some manner utilize the antigen-antibody interaction to detect and/or quantify the amount of a particular antibody that is present in a test sample to assist in diagnosis of disease. There are many such immunoassays known to those of skill in the art. As used herein, however, the antigens and DNA of this disclosure may be substituted for the corresponding reagents in the otherwise known assays, whereby the modified assays may be used to detect and/or quantify autoantibodies that were heretofore difficult or not possible to detect. It is the use of these reagents, the antigens and DNA, that permit modification of known assays for detection of autoantibodies associated with autoimmune myositis or related conditions to help in diagnosis. Such assays include, but are not limited to ELISAs, immunodiffusion assays, and immunoblots. Suitable methods for practicing any of these assays are known to those of skill in the art. Typical protocols for conducting ELISAs, immunoblots, and immunoprecipitation assays are described in the Examples.

As used herein, the antigen, or a protein that includes at least one epitope of the antigen, can be used as the diagnostic reagent. The diagnostic reagents prepared in accordance with this disclosure may be substituted for bovine thymus extracts, HeLa cell extracts or any other antigenic reagent known to those of skill in the art of immunodiagnostic assays for the detection of anti-Mi-2 and anti-PM-Scl antibodies. An epitope is defined as a portion of a protein, polypeptide or peptide that is specifically recognized by an antibody. It may consist of any number of amino acids and it may be dependent upon the primary, secondary or tertiary structure of a protein. In accordance with this disclosure, a protein or peptide that includes at least one epitope of the Mi-2 or PM-Scl antigen, may be used as reagents in the immunodiagnostic assays. For example, the DNA set forth in FIG. 1 encodes a protein that includes at least one Mi-2 epitope. Accordingly, such protein or product produced by expressing the cloned DNA may be used in an assay that utilizes the specific interaction between an anti-Mi-2 autoantibody and such protein.

As used herein, a protein or peptide that includes at least one epitope may contain any sequence of amino acids as long as it includes a portion that has the primary, secondary or tertiary structure that is recognized by a particular antibody. Experimental and computational methods whereby such epitopes may be identified are known to those of skill in the art. Methods and algorithms whereby such epitopes may be identified are known to those of skill in the art. Also encompassed within this class of proteins or peptides is any modifications of such proteins or peptides that do not substantially alter the specificity and extent of the interaction between such protein and the antibody.

As used herein, myositis antigens refer to antigens that are the target of myositis-associated autoantibodies. These antigens may be used to detect these antibodies, thereby assisting in diagnosing autoimmune myositis. Any protein that includes at least one such epitope is encompassed by the term myositis-specific antigen.

As used herein, the DNA falling within the scope of this disclosure is any DNA that encodes a protein including one or more epitopes present on Mi-2 or PM-Scl antigens. The DNA may be genomic DNA, in which case it may include introns, or it may be cDNA which is prepared in vitro from mRNA using a reverse transcriptase and which contains open reading frames. Methods for isolation, cloning or synthesizing DNA and cDNA are well known to those of skill in the art. Expression refers to the process by which nucleic acid is transcribed and translated into peptides, polypeptides, or proteins. If the nucleic acid is derived from genomic DNA, expression may, if an appropriate eukaryotic host cell or organism is selected, include splicing of the mRNA and subsequent glycosylation. An expression vector refers to a recombinant DNA or RNA construct, such as a plasmid, a phage, recombinant virus or other vector that, upon introduction into appropriate host cells, is capable of transcribing nucleic acid molecules which have been cloned into the vector, and then translating the transcribed nucleic acid into a polypeptide. The nucleic acid molecule is cloned into the vector in such a manner that it is operably linked to regulatory sequences that are capable of effecting expression of the heterologous nucleic acid molecules. Upon expression in a selected host cell or organism, if the appropriate regulatory sequences are operably linked to the DNA or included in the heterologous DNA, the expression product may be exported to the cytoplasm and/or may be secreted out of the host cell.

Appropriate expression vectors are well-known to those of skill in the art and include those that are replicable in eukaryotic cells and/or prokaryotic cells. Such expression vectors may remain episomal or may integrate into the host cell genome.

As used herein, a DNA probe is a DNA molecule that includes a sufficient number of nucleotides to specifically hybridize under non-stringent conditions to DNA or RNA that includes complementary sequences of nucleotides. A probe may include any number of nucleotides and may include as few as about 10 and as many as hundreds of thousands of nucleotides. The conditions and protocols for such hybridization reactions are well-known to the those of skill in the art, as are the effects of probe size, temperature, degree of mismatch, salt concentration and other parameters on the hybridization reaction. For example, the lower the temperature and higher the salt concentration at which the hybridization reaction is carried out, the greater the degree of mismatch that may be present in the hybrid molecules.

As used herein, all assays and procedures, such as hybridization reactions and antibody-antigen reactions, unless otherwise specified, are conducted under conditions recognized by those of skill in the art as standard conditions.

The following examples are included for illustrative purposes only and are not intended to limit the scope of the invention.

EXAMPLE 1

Immunoprecipitation and characterization of the human Mi-2 antigen.

Sera with anti-Mi-2 were obtained from patients with dermatomyositis and were part of the collection of myositis sera at the Oklahoma Medical Research Foundation (OMRF). The sera were identified as having the Mi-2 antibody by identity in Ouchterlony immunodiffusion (ID) against bovine thymus extract with a reference serum that had been confirmed using the original Mi prototype serum. Sera from normal laboratory workers were used as controls. Disease control samples from patients without anti-Mi-2 were also taken from the OMRF serum collection. Reference sera for other autoantibodies were also confirmed by ID.

HeLa cell extract was prepared by labeling $2 \times 10^6$ cells (one small 25 cm$^2$ flask) with 500 µCi of $^{35}$S-Met in 2.5 ml of met-deficient minimal essential media with 10% fetal calf serum for 16 hours. The cells were removed with trypsin, pelleted, washed with phosphate buffered saline (PBS), and then resuspended in lysis buffer (NET-2 with 1% NP-40). After centrifugation at 10,000× g for 15 min, the supernatant was added to the IgG coated beads. One flask provided extract for ten samples.

25 µl of patient serum was incubated with 30 Al of a 1:1 (v/v) suspension of preswollen protein A-agarose (Boehringer-Mannheim) in 500 µl of immunoprecipitation buffer containing 10 mM Tris-HCl pH 8.0, 0.5 M NaCl, and 0.1% NP-40 for 2 hours at 4° C. The beads were then washed three times with 50 mM Tris-HCl pH 7.4, 150 mM NaCl, 0.05% NP-40 prior to incubation with extract. The washed immunoprecipitates were suspended in sample buffer, containing 0.2% SDS and 5% mercaptoethanol, heated at 100° C. for 5 minutes and were analyzed by electrophoresis on a SDS-10% polyacrylamide gel prepared according to the method of Laemmli, *Nature* 227: 680 (1970), using a discontinuous buffer system. The gels were developed by autoradiography.

Immunoprecipitates from the HeLa extract using anti-Mi-2 sera were run on the gel and compared to immunoprecipitates using normal human serum and sera known to contain the autoantibodies OJ (antibody to isoleucyl-tRNA synthetase), PL-12, Ro,La, and PL-7, but not Mi-2.

The autoradiograms were exposed for 48 hours in order to detect the distinct pattern of proteins immunoprecipitated by anti-Mi-2. Although the bands were weak and often difficult to distinguish from background or artifact, comparison of immunoprecipitates obtained using multiple positive sera, revealed a characteristic pattern. A series of 5 bands of 249, 198, 152, 67, and 62 kDa, which were called a, a', b, c, and d, respectively, was precipitated by 10 different anti-Mi-2 containing-sera. None of the three high molecular weight bands (a, a', and b) was seen in parallel lanes from normal or other myositis sera. Control sera that contained other autoantibodies immunoprecipitated the characteristic proteins of those autoantibodies, but did not precipitate proteins that corresponded to those immunoprecipitated by anti-Mi-2 sera.

EXAMPLE 2

Purification of the Bovine Mi-2 antigen from Bovine thymus extract.

Fresh or frozen bovine thymus was homogenized in 2 volumes of cold PBS (10 mM phosphate buffer pH 7.2, 150 mM NaCl, 10 mM Na Azide) with 1.3 mM phenylmethylsulfonyl fluoride (PMSF) and. 1.3 mM dithiothreitol (DTT) and extracted for 30 min. The homogenate was then centrifuged at 12210× g for 2 hours, and the supernatant was filtered through cheesecloth.

The filtered supernatant was diluted with 2 volumes of 10 mM sodium phosphate buffer, pH 7.0 and then incubated with similarly equilibrated DEAE-cellulose (Whatman) for 1 hour. The resin was washed in a sintered glass funnel with 10 mM phosphate buffer, pH 7.0, and then with 0.1 M NaCl in 10 mM phosphate buffer pH 7.0. The antigen was then eluted with 0.2 M NaCl in phosphate buffer.

Antigenic activity was assayed by standard and inhibition enzyme linked immunosorbent assay (ELISA) and it eluted between 0.1 M and 0.2 M NaCl. Protein concentration was determined by the method of Bradford ((1976) *Anal. Biochem.* 72: 248) using the Bio-Rad Protein (Richmond, Calif.) assay.

Two affinity adsorbents were prepared, each with the IgG fraction from a different sample that previously had been determined by ID and ELISA to have anti-Mi-2 autoantibodies. Plasma from one of the patients was provided by Dr. Frank Arnett of the University of Texas Health Sciences Center at Houston. The other patient whose plasma was used was treated at the University of Oklahoma Health Sciences Center. The IgG fraction of the anti-Mi-2 plasma was purified by DEAE™-cellulose chromatography (DEAE 52, Whatman). About 35 ml of plasma from each of the selected sera were loaded on the DEAE-cellulose, which at been equilibrated to pH 7.0. The flow-through fractions that contain protein (measured by absorbance at 280 nm) were pooled, concentrated and dialyzed against 0.1 M bicarbonate buffer, pH 8.3 with 0.5 M NaCl. About 65–70 mg of IgG were obtained from each 35 ml of plasma. The IgG was coupled at 5 mg IgG/ml gel to cyanogen bromide preactivated Sepharose™ 4B (Pharmacia, Uppsala Sweden) according to the manufacturer's instructions.

Greater than 90% coupling was achieved. The immunosorbent gel was then washed alternately with 0.1 M acetate pH 4.0 and 0.1 M NaHCO$_3$, pH 9.0, for three cycles followed by washing with 4 M MgCl$_2$. The gel was then equilibrated with TBS (50 mM Tris-ECl pH 7.2,0.5 M NaCl, 10 mM Na Azide) and packed in a column prior to use.

The thymus extract fractions from the DEAE column that contained Mi-2 antigenic activity, the 0.2 M NaCl eluate, were then loaded onto one of the two immunoaffinity resins, which was then washed with 2 l of TBS until the absorbance of the flow through at 280 nm was below 0.05 units. Two column volumes of 4 M MgCl$_2$ were then applied to the column. Elution of the immunoaffinity chromatography column with 4 M MgCl$_2$ yielded a single broad protein peak. The fractions were pooled and dialyzed against 10 mM Tris-HCl pH 7.0, and concentrated to approximately 1 mg/ml. The affinity purified antigen retained maximal activity in ELISA at protein concentrations of 3 $\mu$g/ml and higher.

EXAMPLE 3

Analysis of the bovine and human Mi-2 antigens.

SDS-PAGE analysis, performed as described in Example 1, of the affinity purified bovine Mi-2 antigen revealed several bands. The relative intensity of the bands varied in different preparations, but the higher molecular weight bands at 250, 240, and 145 kDa were consistently fainter than the bands at 94, 65, and 40 kDa, while the 40 kDa band was usually the strongest. No bands corresponding to bands e or g were seen in the lanes in which the $^{35}$S-immunoprecipitated human antigen were loaded (see Example 1), but the 250, 240, 145 and 65 kDa bands were similar to those seen by immunoprecipitation.

Western blots of the purified bovine antigen were run against anti-Mi-2 sera. Samples of the purified antigens were run on Laemnli gels as described in Example 1. The separated sample was then transferred to nitrocellulose in a Bio-Rad Trans-Blot apparatus (Bio-Rad, Laboratories, Richmond, Calif.) in 0.025 M Tris-0.192 M glycine buffer at pH 8.3 with 20% methanol.

Prior to binding the anti-Mi-2 serum, the nitrocellulose paper was blocked with 5% bovine dry non-fat milk in 0.010 M Tris, 0.15 M NaCl, pH 7.4, for 1 hr at 40° C. The anti-Mi-2 serum was diluted 1/100 in 5% bovine dry non-fat milk in 0.010 M Tris, 0.15 M NaCl, pH 7.4, and was reacted at room temperature for 2 hrs or overnight at 4° C. with the nitrocellulose filters.

A conjugate of goat anti-human IgG/alkaline phosphatase (Sigma) diluted 1/500 in buffer was then applied. After washing, the nitrocellulose strip was placed in alkaline phosphatase substrate for 10 to 20 min and finally washed with methanol/water mixture. Silver staining was performed using the BioRad Silver Stain Kit (Richmond, Calif.).

Western blotting of the immunoaffinity purified antigen was consistently negative when developed with sera containing anti-Mi-2. Silver staining of the gel following transfer to nitrocellulose showed incomplete transfer of the 250, 240 and 145 kDa bands under all of the transfer conditions attempted. When partial transfer of these bands was achieved, the staining with patient sera remained negative. Western blotting against whole HeLa extract was also negative with all monospecific anti-Mi-2 sera tested. These results suggest that the epitope or epitopes in both the bovine and human Mi-2 antigen that are recognized by the anti-Mi-2 autoantibody in patient sera is dependent upon the secondary and/or tertiary structure of the subunits of the antigen.

EXAMPLE 4

Subunit analysis of the affinity-purified bovine Ni-2 antigen.

The affinity-purified Mi-2 bovine antigen was analyzed using Superose™-12 gel filtration chromatography on a fast protein liquid chromatography (FPLC) apparatus (Pharmacia). Approximately 50 $\mu$g of immunoaffinity purified Mi-2 from bovine thymus was applied to a Superose™-12 10/30 gel filtration column, which had been equilibrated in 150 mM NaCl in 15 mM Tris-HCl buffer, pH 7.2, and eluted with the same buffer.

Typically four protein peaks, A, B, C, and D, eluted from the Superose™-12 column. The relative size of the peaks that eluted varied with different antigen preparations, but four peaks consistently eluted. Peak A eluted with the void volume (molecular weight greater than 2×10$^6$ Da). Peak B generally eluted approximately 1.5 ml after the first peak. The shape and position of peaks C and D were more variable. ELISA activity against anti-Mi-2 serum was detected consistently in peak A, and in some runs all activity eluted in this peak. In other runs, however, activity eluted in all peaks.

Eluted fractions from peaks A, B, and D and unfractionated immunoaffinity purified antigen were analyzed on an SDS-10% polyacrylamide gel and stained with silver stain. The SDS-PAGE gels of fractions from individual peaks showed partial segregation of the different molecular weight bands that were seen in the whole affinity purified antigen. Peak A always contained bands with molecular weights 250, 240, 145, and 40 kDa. Peak B contained the 94 kDa band, and sometimes 250, 240, 145, and 40 kDa bands were also seen. Peak C contained small amounts of bands with molecular weights 94, 65, and 40 kDa. Peak D contained the 65 kDa band and sometimes a small amount of the 40 kDa band.

The affinity-purified Mi-2 bovine antigen was also applied to a MonoQ™ HR 5/5 anion exchange column (Pharmacia, Piscataway, N.J.), which had been equilibrated in 10 mM phosphate buffer, pH 7.0, and then washed extensively with the same buffer. The column was eluted with a linear gradient of 0–1000 mM NaCl in 10 mM phosphate buffer, pH 7.0. Fractions were collected and either tested for antigenic activity by ELISA with known anti-Mi-2 sera as controls, or analyzed on SDS-PAGE.

The elution profile from the Mono-Q FPLC column showed a large number of small peaks over a broad elution range, but the larger peaks between 0.38 and 0.48 M NaCl contained activity as measured by ELISA. Maximum activity eluted in the peak at 0.43 M NaCl. SDS-PAGE of the eluted fractions demonstrated partial separation of the bands found in whole affinity antigen. The 65 kDa band was seen in fractions that eluted between 0.2–0.35 M NaCl. The 250, 240, 145 and 40 kDa bands eluted in fractions from 0.4 to 0.45 M NaCl, including the peak with greatest ELISA activity. This was consistent with the results from the gel filtration. In the fraction that eluted at 0.45–0.47 M NaCl, the 94 kDa band and an additional band of 85 kDa were eluted and were visible on SDS-PAGE. There was also a small amount of the 40 kDa band in this fraction. SDS-PAGE of the other fractions did not show any visible bands.

EXAMPLE 5
Cloning of DNA that encodes the human Mi-2 antigen.

A human thymocyte lambda $gt_{11}$ expression library (Clontech) was expressed in *E. coli* Y1090 and was screened with serum from a dermatomyositis patient. This serum had previously been tested by immunoprecipitation and by Ouchterlony, using bovine thymus extracts, for the presence of autoantibodies. The only autoantibodies that it contained were anti-Mi-2 autoantibodies.

Two cDNA clones, L1 and L2, were selected that expressed protein that reacted with the anti-Mi-2 serum, but that did not react with serum from normal controls or with serum obtained from a dermatomyositis patient that contained autoantibodies other than anti-Mi-2.

A second lambda $gt_{11}$ expression library, a HeLa library, was similarly screened and two clones, L3 and L4, were selected which also reacted specifically with anti-Mi-2 serum.

Clone L1 was then used to screen sera from 40 patients. These sera had previously been shown to be positive for the anti-Mi-2 autoantibody. All of the 40 samples reacted specifically with clone L1. Control myositis patients and normals were all negative.

Each of the four clones were then characterized. The cloned DNA was expressed, and the proteins were blotted onto nitrocellulose. Serum containing the anti-Mi-2 antibody was then incubated with the nitrocellulose with proteins from one of the clones (L4). The bound antibody was eluted and tested against the nitrocellulose strips on which the other clones had been blotted. Each of the other three clones reacted similarly with the eluted antibody, which indicates that each of the clones encodes the same epitope (s). In view of the similar reactivity and size (each of the inserts was 1.1 kB), the four clones are most likely identical.

The insert from one of the clones was completely sequenced. The nucleotide sequence is shown in FIG. 1. The 1.1 kB insert includes a single long open reading frame that spans the entire insert, in phase with the beta-galactosidase. Other reading frames are either too small to encode a conformational epitope and/or are not in phase with beta-galactosidase. Since there are no start or stop codons, the 1.1 kB insert does not include the entire gene.

TABLE 2

Amino acid and codon frequency analysis of the cloned human Mi-2 fragment

| amino acid | Codon and number | | | | | | total | % |
|---|---|---|---|---|---|---|---|---|
| Ala | (GCT)3 | (GCC)7 | (GCA)3 | (GCG)1 | | | 14 | 3.99 |
| Arg | (CGT)4 | (CGC)3 | (CGA)4 | (CGG)6 | (AGA)2 | (AGG)2 | 21 | 5.98 |
| Asn | (AAT)3 | (AAC)3 | | | | | 6 | 1.71 |
| Asp | (GAT)13 | (GAC)12 | | | | | 25 | 7.12 |
| Cys | (TGT)7 | (TGC)11 | | | | | 18 | 5.13 |
| Gln | (CAA)2 | (CAG)8 | | | | | 10 | 2.85 |
| Glu | (GAA)14 | (GAG)32 | | | | | 46 | 13.11 |
| Gly | (GGT)5 | (GGC)14 | (GGA)6 | (GGG)8 | | | 33 | 9.40 |
| His | (CAT)3 | (CAC)10 | | | | | 13 | 3.70 |
| Ile | (ATT)5 | (ATC)6 | (ATA)0 | | | | 11 | 3.13 |
| Leu | (TTA)0 | (TTG)1 | (CTT)5 | (CTC)2 | (CTA)5 | (CTG)10 | 23 | 6.55 |
| Lys | (AAA)6 | (AAG)22 | | | | | 28 | 7.98 |
| Met | (ATG)5 | | | | | | 5 | 1.42 |
| Phe | (TTT)2 | (TTC)3 | | | | | 5 | 1.42 |
| Pro | (CCT)12 | (CCC)8 | (CCA)9 | (CCG)1 | | | 30 | 8.55 |
| Ser | (TCT)0 | (TCC)5 | (TCA)3 | (TCG)1 | (AGT)4 | (AGG)3 | 16 | 4.56 |
| Thr | (ACT)0 | (ACC)3 | (ACA)1 | (ACG)1 | | | 5 | 1.42 |
| Trp | (TGG)9 | | | | | | 9 | 2.56 |
| Tyr | (TAT)4 | (TAC)9 | | | | | 13 | 3.70 |
| Val | (GTT)2 | (GTC)8 | (GTA)3 | (GTG)7 | | | 20 | 5.70 |
| STOP | (TAA)0 | (TAG)0 | (TGA)0 | | | | | | molecular weight = 39973
number of amino acids = 351
Arg + Lys = 49
Asp + Glu = 71

EXAMPLE 6
Cloning DNA that encodes the human PM-Scl antigen.

20 samples of sera that had been shown to contain the anti-PM-Scl antibody by immunoprecipitation and immunodiffusion against bovine thymus extract were tested for reactivity with HeLa cell extract in Western blot. HeLa cell extract was prepared as described in Example 1. The Western blots were performed as described in Example 3. 14 of the tested sera stained the 100 kDa band; 9 sera stained the 70 kDa band in addition to the 100 kDa band; 1 of the 20 sera stained only the 70 kDa band; 2 stained only other bands and 3 were negative,.

Several of the tested sera that stained both the 100 kDa band and the 70 kDa band were selected for screening a human library in order to obtain cDNA that encodes the PM-Scl antigen.

A human thymocyte lambda $gt_{11}$ cDNA expression library was screened with the selected sera for clones that encode the PM-Scl antigen, as described in example 5. Two clones, JH 2 and JH 3, that reacted with multiple anti-PM-Scl sera were selected.

The selected clones were then reacted with 41 samples of sera that contain anti-PM-Scl antibodies; 20 samples of sera that contain other autoantibodies, and 6 samples from normal volunteers. 33 of the 41 samples of anti-PM-Scl sera reacted with both clones. 26 of the 33 reacted very strongly. None of the 20 sera that contained other autoantibodies reacted nor did any of the 6 sera samples of normal control sera.

Plaques of cloned and wild type phage on nitrocellulose were incubated with an anti-PM-Scl serum that reacted with both the 100 and 70 kDa bands. Antibody that was eluted from the nitrocellulose stained the 100 kDa band, but did not stain the 70 kDa band.

A partial nucleotide sequence derived from the ends of the 2.5 kB insert in clone JH2 is set forth in FIG. 2. FIGS. 3 is a restriction enzyme map of clone JH2 showing the location of cleavage sites for TaqI, KpnI, XhoI, SmaI, and PstI. Fragments from double digestions with KpnI and TaqI; and XhoI and PstI, are defined. The fragments were isolated from agarose gels and inserted into M13. The M13 with complementary strands of the indicated fragments were identified using complementarity tests and these fragments were partially sequenced. Preliminary sequences from individual fragments are shown in FIG. 4.

Modifications and variations of the present invention, myositis-specific antigens, and nucleic acid sequences encoding all or a portion thereof, and methods of use thereof, will be obvious to those skilled in the art from the foregoing detailed description. Such modifications and variations are intended to come within the scope of the appended claims.

We claim:

1. An isolated nucleic acid molecule, consisting essentially of the sequence shown in FIG. 1 that encodes all or a peptide portion of an Mi-2 protein, wherein the protein expressed from said nucleic acid molecule includes at least one epitope of said protein that is bound by a myositis-specific autoantibody.

2. The nucleic acid molecule of claim 1, labelled for use as a probe, wherein said probe hybridizes to a nucleic acid sequence that encodes an Mi-2 antigen.

3. An isolated nucleic acid molecule, consisting essentially of twenty-four consecutive nucleotides of the sequence shown in a sequence selected from the group consisting of the sequences shown in FIG. 2A, FIG. 2B, FIG. 4A, FIG. 4B, FIG. 4C, FIG. 4D and FIG. 4E, that encodes all or a peptide portion of a myositis specific PM-Scl protein, wherein the protein expressed from said sequence includes at least one epitope of PM-Scl that is bound by a myositis-specific autoantibody.

4. The nucleic acid molecule of claim 3 labelled for use as a probe, wherein said probe hybridizes to a nucleic acid sequence that encodes a PM-Scl antigen.

5. A nucleic acid molecule for use as a probe consisting essentially of a sequence of at least 10 nucleotides of the sequence shown in FIG. 1, wherein the molecule specifically hybridizes under non-stringent conditions to a nucleic acid molecule that encodes an Mi-2 antigen.

6. The nucleic acid molecule of claim 5, labelled with a detectable label.

7. A nucleic acid molecule for use as a probe consisting essentially of a sequence of at least 10 nucleotides of a sequence selected from the group consisting of the sequences shown in FIG. 2A, FIG. 2B, FIG. 4A, FIG. 4B, FIG. 4C, FIG. 4D and FIG. 4E, wherein the molecule specifically hybridizes under non-stringent conditions to a nucleic acid molecule that encodes a PM-Scl antigen.

8. The nucleic acid molecule of claim 7 labelled with a detectable label.

* * * * *